(12) United States Patent
      Cohen

(10) Patent No.: US 12,635,856 B2
(45) Date of Patent: May 26, 2026

(54) ELONGATED BODY SHEATH ASSEMBLIES, IMAGING ELEMENT CLEANING APPARATUSES COMPRISING SAME AND METHODS OF ASSEMBLING AND USING SAME

(71) Applicant: ClearCam, Inc., Austin, TX (US)

(72) Inventor: Alexander Ross Cohen, Austin, TX (US)

(73) Assignee: ClearCam, Inc., Austin, TX (US)

( * ) Notice: Subject to any disclaimer, the term of this patent is extended or adjusted under 35 U.S.C. 154(b) by 299 days.

(21) Appl. No.: 18/261,611

(22) PCT Filed: Feb. 7, 2022

(86) PCT No.: PCT/US2022/015494
     § 371 (c)(1),
     (2) Date: Jul. 14, 2023

(87) PCT Pub. No.: WO2022/173699
     PCT Pub. Date: Aug. 18, 2022

(65) Prior Publication Data
     US 2024/0108200 A1      Apr. 4, 2024

Related U.S. Application Data

(60) Provisional application No. 63/149,318, filed on Feb. 14, 2021.

(51) Int. Cl.
     *A61B 1/00*      (2006.01)
     *A61B 1/12*      (2006.01)

(52) U.S. Cl.
     CPC .......... *A61B 1/00135* (2013.01); *A61B 1/126* (2013.01)

(58) Field of Classification Search
     CPC . A61B 1/00135; A61B 1/126; A61B 1/00142; A61M 25/0021; A61M 25/0023; A61M 25/0662; A61M 2025/0675
     See application file for complete search history.

(56) References Cited

U.S. PATENT DOCUMENTS

2006/0258904 A1* 11/2006 Stefanchik ......... A61B 1/00073
                                                   600/153

* cited by examiner

*Primary Examiner* — Timothy J Neal
(74) *Attorney, Agent, or Firm* — David O. Simmons; IVC Patent Agency

(57) ABSTRACT

A sheath assembly comprises a sheath including an outer wall having an interior surface defining a central passage extending along a length of the outer wall. A cross-sectional profile of the central passage is jointly defined by a generally round portion and a tapered portion extending contiguously therefrom. The outer wall has an access opening extending therethrough that extends through a tip of tapered portion. A mounting body attached to an end portion of the sheath adjacent to the access opening is engageable with a mating mounting body. An elongated member is within the central passage. A first end portion of the elongated member extends through the access opening such that a first end of the elongated member is external to the central passage. A second portion of the elongated member between the access opening and a second end of the elongated member is located within the central passage.

30 Claims, 7 Drawing Sheets

ELONGATED BODY SHEATH ASSEMBLIES, IMAGING ELEMENT CLEANING APPARATUSES COMPRISING SAME AND METHODS OF ASSEMBLING AND USING SAME

CROSS-REFERENCE TO RELATED APPLICATIONS

This international (PCT) application claims priority from co-pending United States Provisional Patent Application having Ser. No. 63/149,318, filed 14 Feb. 2021, entitled "ELONGATED BODY SHEATH ASSEMBLIES, IMAGING ELEMENT CLEANING APPARATUSES COMPRISING SAME AND METHODS OF ASSEMBLING AND USING SAME", which has a common applicant herewith and being incorporated herein in its entirety by reference.

FIELD OF THE DISCLOSURE

The disclosures made herein relate generally to approaches for engaging associated devices and, more particularly, to elongated body sheath assemblies, to imaging element cleaning apparatuses comprising same and to methods of assembling and using same.

BACKGROUND

There are many types of operational procedures that require visualization of structures located within an enclosed cavity of a body of material (i.e., a body cavity). Such operational procedures are known to use an imaging device having a portion thereof that is insertable into the body cavity for acquiring imaging information of structures within the body cavity. A prime example such an operational procedure is a surgical procedure that requires imaging within a body cavity of a patient.

As shown in FIG. 1, a visualization scope 1 (i.e., an imaging device) used in robotic surgical procedures is characterized as having a system interface portion 5 and an extension portion 10 connected at its proximate end 15 to the system interface portion 5. The extension portion 10 has an imaging element 20 such as a lens at its distal end portion 25. The imaging element 20 may have an exposed surface that is generally flush with or that defines an end face of the extension portion 10. The imaging element 20 is connected to an image transmission element (e.g., an optical fiber or other image transmitting element) that is internal to the extension portion 10. The image transmission element extends along the length of the extension portion 10 and terminates at an image information output unit 30 connected to the system interface portion 5, the extension portion 10 or both. The image information output unit 30 enables the imaging element 20 to be connected to an image output apparatus (e.g., a visual display console of a robotic surgical system) through which target surgical sites visible to the imaging element 20 may be viewed by surgery personnel. Examples of commercially available visualization scopes (e.g., robotic or otherwise) include, but are not limited to, visualization scopes manufactured under brand names of KARK STORZ®, LINVATEC®, OLYMPUS®, RICHARD WOLF®, STRYKER® and INTUITIVE SURGICAL®.

During a surgical procedure using the visualization scope 1, the exposed surface of the imaging element 20 may become impaired due to one or more in-vivo scenarios. Examples of these scenarios include the exposed surface of the imaging element 20 becoming fogged with moisture within the surgical space, or the exposed surface of the imaging element 20 may be smeared by blood, fat or other bodily fluids or tissues (e.g., interstitial fluid, fat tissue or the like). To maintain required visualization of target surgical sites, it is desirable to clean the exposed surface of the imaging element 20 while the distal end portion of the extension portion 10 remains in the surgical site.

Various apparatuses have been devised to clean an exposed surface of an imaging element of an imaging device while the distal end portion of the device remains in a concealed operation site. In some implementations, such cleaning apparatuses are configured as an article of manufacture that is selectively mountable on a commercially available visualization scope (i.e., a scope-mountable cleaning apparatus). Examples of cleaning apparatuses specifically adapted for use with visualization scopes and the like are disclosed in the following United States patents and patent application publications, all of which are incorporated herein in their entirety by reference: US20160128551, US20090229067, U.S. Ser. No. 10/791,918, U.S. Pat. Nos. 9,050,036, 8,979,738, 7,959,561, 6,923,759, 6,755,782 and 5,518,502.

It is well known that commercialization of imaging element cleaning apparatuses must meet requirements related to precision of construction/operability, cost of fabrication, multi-device/brand compatibility and end-user value. Therefore, techniques for manufacturing and configuring components of imaging element cleaning apparatuses in a manner that benefits precision of construction/operability, cost of fabrication, multi-device/brand compatibility and end-user value would be advantageous, desirable and useful.

SUMMARY OF THE DISCLOSURE

Embodiments of the disclosures made herein are directed to elongated body sheath assemblies. More specifically, embodiments of the disclosures made herein are directed to elongated body sheath assemblies adapted for use with imaging element cleaning apparatuses and to techniques for manufacturing and configuring such elongated body sheath assemblies in a manner that benefits precision of construction/operability, cost of fabrication, multi-device/brand compatibility and end-user value. Such configuring of components may be implemented, for example, during manufacturing, during pre-surgery preparation, during surgery and the like. The aforementioned beneficial attributes serve to aid in the commercialization of imaging element cleaning apparatuses. For example, embodiments of the disclosures made herein may be configured in a manner that permits a single scope sheath to be used with a plurality of differently-configured cleaning member assemblies (e.g., cleaning member such as a wiper attached to a coupling element such as wire) or other elongated bodies (e.g., optical fiber cable, a cauterizing body, an irrigation tube, a mechanical device control body, and the like) as required or preferred for a given application, mating visualization scope and the like.

In one or more embodiments, a sheath assembly comprises a sheath including an outer wall having an interior surface that defines a central passage extending along a length of the outer wall. A cross-sectional profile of the central passage is jointly defined by a generally round portion and a tapered portion extending contiguously from the generally round portion. The outer wall has an access opening extending therethrough. The access opening extends through a tip of tapered portion. A mounting body is attached to an end portion of the sheath adjacent to the access opening. The mounting body is interlockedly engageable with a mating mounting body.

In one or more embodiments, a bisecting axis of the sheath bisects the access opening and the central passage.

In one or more embodiments, generally flat opposing walls of the tapered portion converge to the tip.

In one or more embodiments, the opposing walls are flat.

In one or more embodiments, the central passage is substantially straight.

In one or more embodiments, a bisecting axis of the sheath bisects the access opening and the central passage.

In one or more embodiments, the central passage is accessible through an opening in the mounting body.

In one or more embodiments, an elongated member is within the central passage, wherein a first end portion of the elongated member extends through the access opening such that a first end of the elongated member is located external to the central passage and a second portion of the elongated member between the access opening and a second end of the elongated member is located within the central passage.

In one or more embodiments, the generally round portion of the sheath is adapted for having an extension portion of a device inserted therein, the tapered portion of the sheath defines an elongated body receiving portion thereof and the generally round portion and the tapered portion are jointly configured for causing insertion of extension portion of the device to urge second portion of the elongated member into the elongated body receiving portion of the central passage.

These and other objects, embodiments, advantages and/or distinctions of the present invention will become readily apparent upon further review of the following specification, associated drawings and appended claims.

BRIEF DESCRIPTION OF THE DRAWINGS

Figure 7:
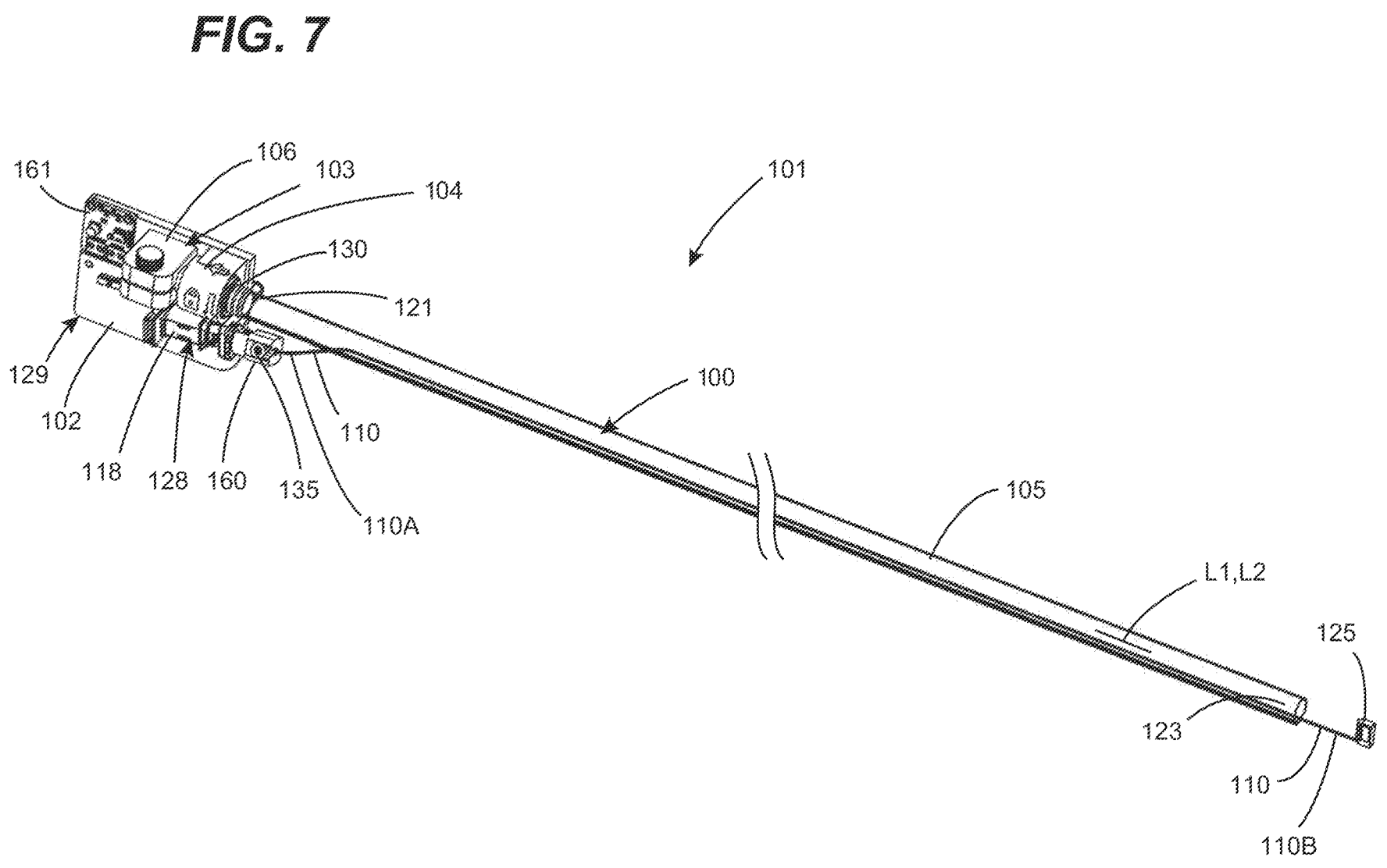

FIG. 7 is a perspective view showing an imaging element cleaning apparatus in accordance with one or more embodiment of the disclosures made herein.

DETAILED DESCRIPTION

Figure 1:
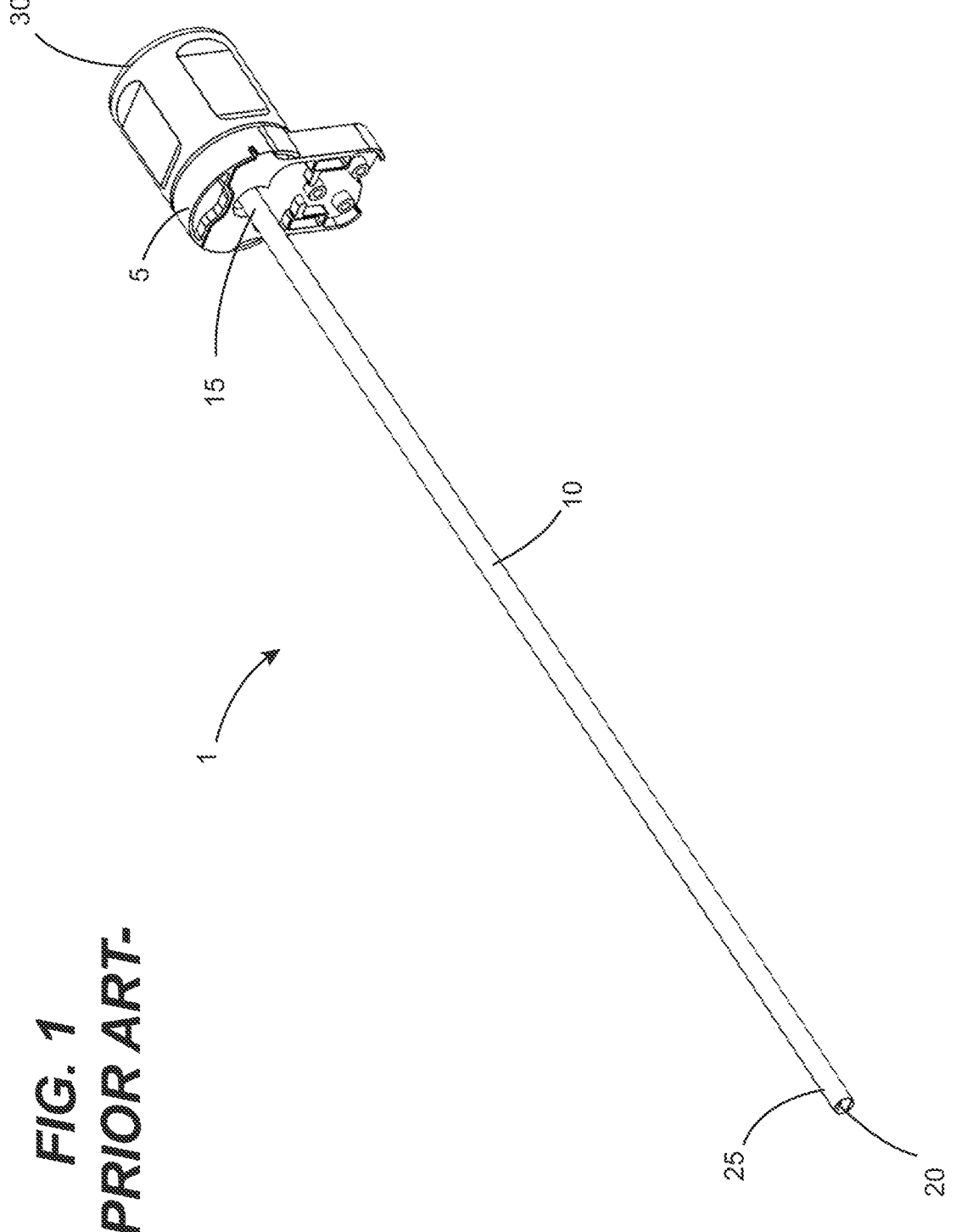
FIG. 1 is a perspective view showing a prior art visualization scope.

FIGS. 2-10 show a sheath assembly 100 in accordance with one or more embodiments of the disclosures made herein. The sheath assembly 100 comprises a scope sheath 105 and a coupling element 110. The coupling element 110 extends within a central passage 115 of the scope sheath 105. The scope sheath 105 may include an access opening 120 at a proximate end portion 121 (i.e., a first end portion) thereof within an outer wall 122 thereof for allowing a proximate end portion 110A (i.e., first end portion) of the coupling element 110 to extend therethrough. The proximate end portion 110A of the coupling element 110 extending through the access opening 120 enables the proximate end portion 110A of the coupling element 110 to be coupled to a mating component of an imaging element cleaning apparatus (e.g., a user interface portion thereof, a drive unit thereof or the like). A distal end portion 110B (i.e., second end portion) of the coupling element 110 extends through an opening of the central passage 115 at a distal end portion 123 (i.e., second end portion) of the scope sheath 105. The distal end portion 110B of the coupling element 110 may have a cleaning member 125 (e.g., a resilient wiper) attached thereto at the distal end portion 110B thereof, thereby forming a coupling element subassembly.

Figures 2A, 2B:
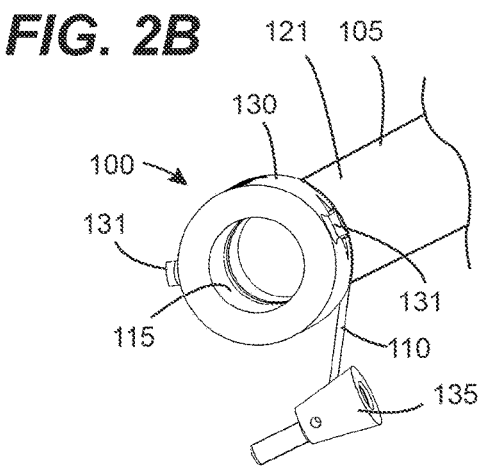
FIG. 2A is a perspective view showing an embodiment of a sheath assembly in accordance with one or more embodiments of the disclosures made herein.
FIG. 2B is an enlarge fragmentary view of an end portion of the sheath assembly of FIG. 2A.

As best shown in FIGS. 2A and 2B, the sheath assembly 100 may be in the form of a "cleaning cartridge" that docks to a manual or robotic drive unit—e.g., device handle or drive unit adapted for use with a robotic surgical system. The sheath assembly 100 comprises a sheath mounting body 130 attached to a first end portion 121 of the scope sheath 105. The sheath mounting body 130 is detachably attachable to a sheath mount of a manual or robotic drive unit (e.g., see sheath mount 104 in FIG. 7-10) such as by pins 131 (i.e., protrusions) that each engage a mating groove (i.e., a mating features for providing an interlocked interface) of the sheath mount. Such mating features may be configured for defining/providing a desired angular "clocking" of the sheath assembly 100 relative to the drive unit. The interlocked interface either alone or in combination with a supplemental interlocking structure (e.g., a spring-loading structure) may be configured to secure the scope sheath 105 in a positionally and rotationally locked configuration relative to the sheath mount.

The sheath assembly 100 may also comprise a coupling element engagement body 135 attached to the proximate end portion 110A of the coupling element 110 such as via a fastener that secures the coupling element at a fixed location along a length of the coupling element 110. The coupling element engagement body 135 may be located on the coupling element 110 at a prescribed distance from the cleaning member 125. As shown, the coupling element engagement body 135 may be embodied as a tapered body. The coupling element engagement body 135 may be selectively and securely engageable with a mating engagement body of a manual actuation device or an actuation device configured for use with a robotic surgical system—e.g., a rotational movement actuator thereof (e.g., see coupling element engagement body 135 in FIGS. 7-10). These engagement arrangements of the scope sheath 105 and the coupling element 110 individually and jointly provide for a simple, yet effective and efficient approach for mechanically securing the sheath assembly 100 to a manual actuation device or an actuation device configured for use with a robotic surgical system.

The scope sheath 105 may be a thin-walled tube made from a metallic, composite and/or polymeric material. The coupling element 110 may be a flexible small-diameter wire, cable, tubular structure or the like made from a metallic, fibrous, polymeric material and/or the like. In some embodiments, the coupling element 110 is characterized by an elongated small diameter structure that offers at least a limited degree of bendability in combination with high torsional rigidity. In other embodiments, the coupling element 110 is characterized by an elongated small diameter structure that offers a given (e.g., predictable) amount of torsional compliance. Based on these characterizing attributes, examples of coupling element 110 include, but are not limited to, solid metallic wire, tube, spiraled metal wire, a polymeric filament(s), a torque coil(s), a composite filament(s) or the like.

Figures 3, 4:
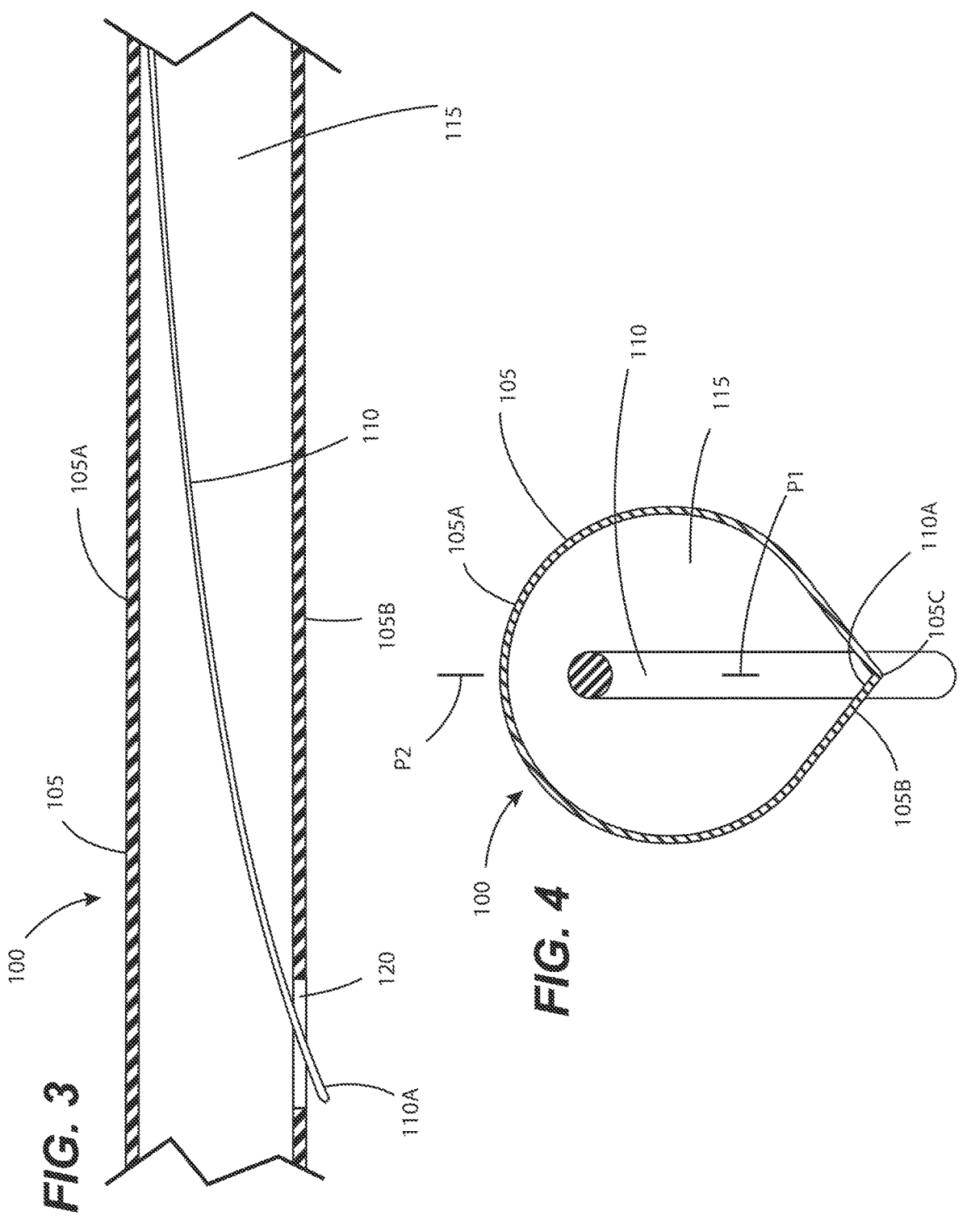
FIG. 3 is a cross-sectional, side, fragmentary view of the sheath assembly of FIG. 2A.
FIG. 4 is a cross-sectional end view of the sheath assembly of FIG. 2A.
Figures 5, 6:
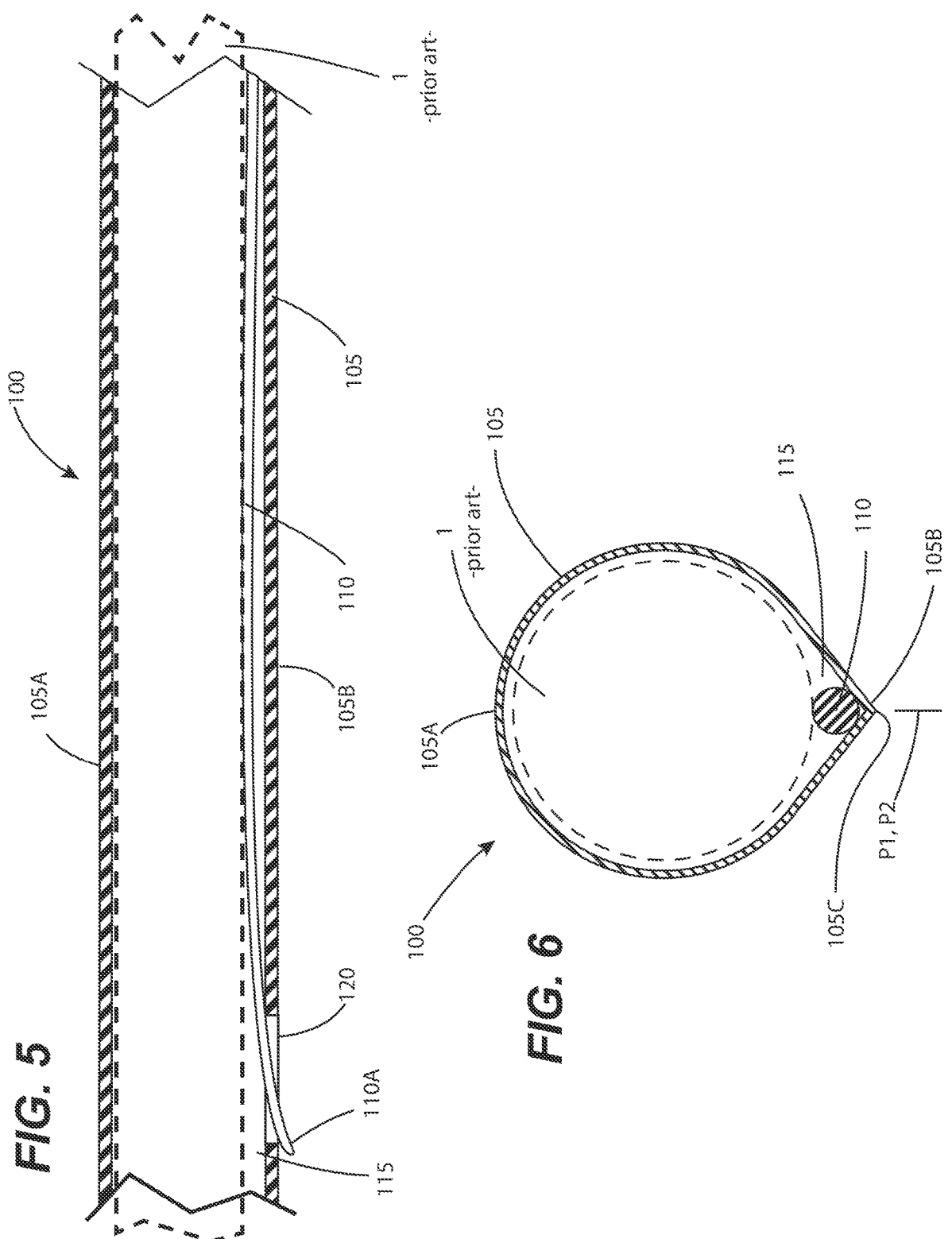
FIG. 5 is a cross-sectional, side, fragmentary view of the sheath assembly of FIG. 2A, where an extension portion of a visualization scope is engaged with the scope sheath of the sheath assembly.
FIG. 6 is a cross-sectional end view of the sheath assembly of FIG. 2A, where an extension portion of a visualization scope is engaged with the scope sheath of the sheath assembly.
Figure 8:
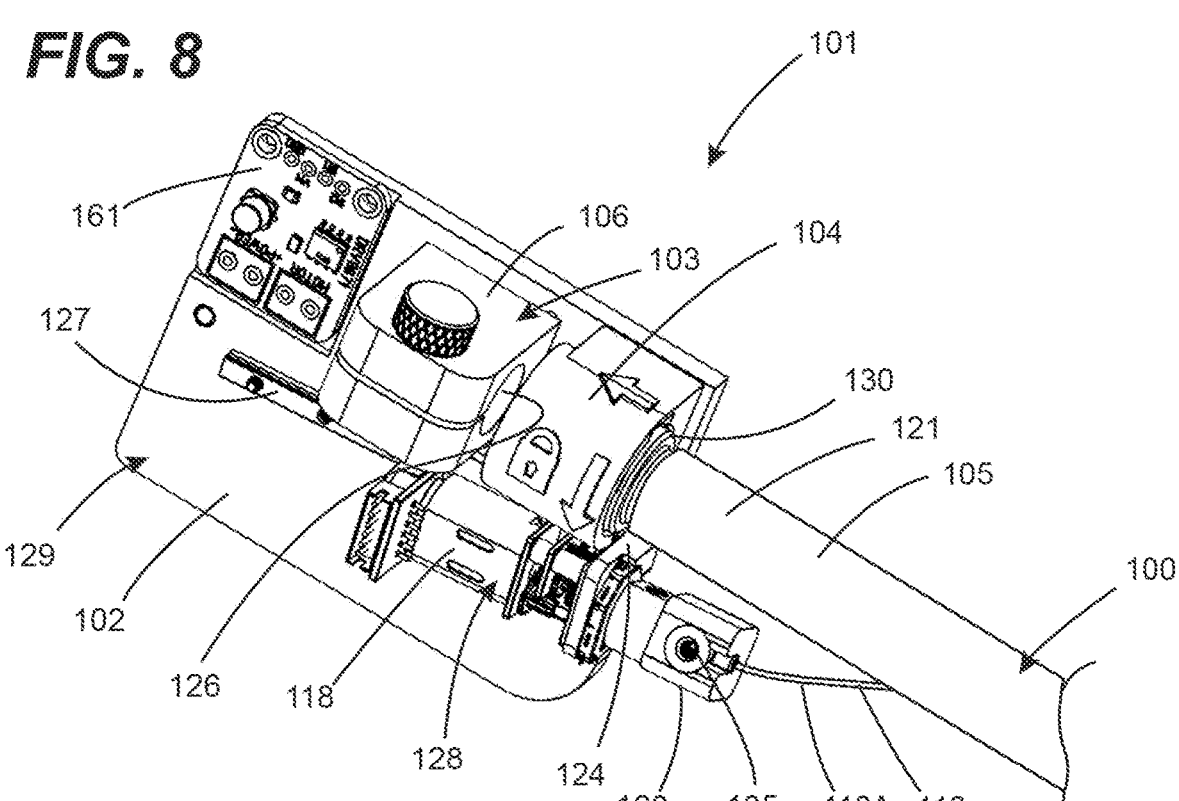
FIG. 8 is a first enlarged partial perspective view of the imaging element cleaning apparatus of FIG. 7.
Figure 9:
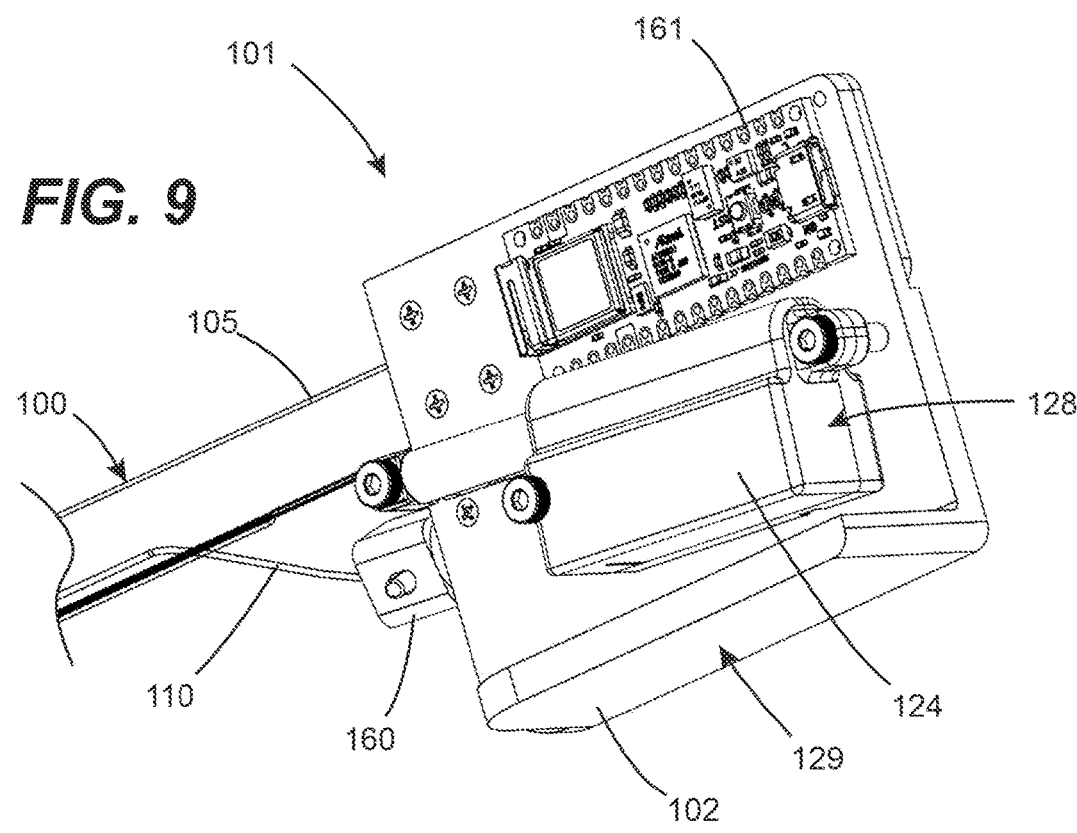
FIG. 9 is a second enlarged partial perspective view of the imaging element cleaning apparatus of FIG. 7.
Figure 10:
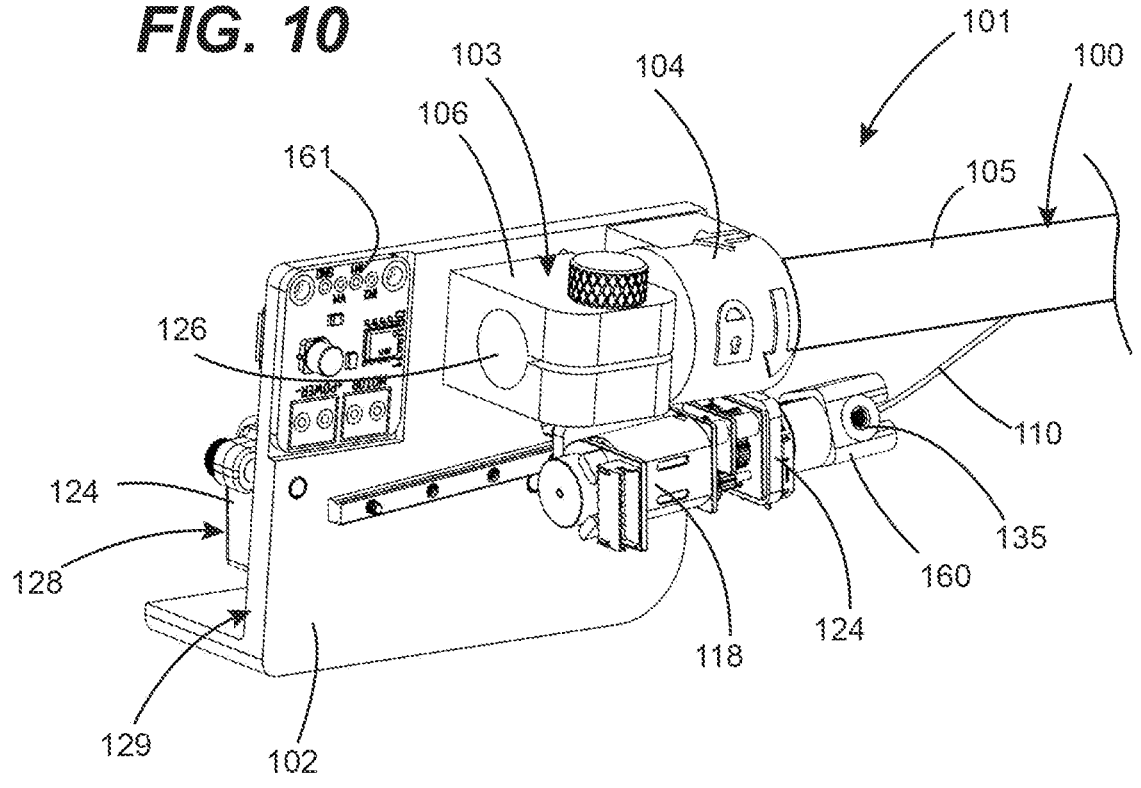
FIG. 10 is a third enlarged partial perspective view of the imaging element cleaning apparatus of FIG. 7.

Referring now to FIGS. 3-6, in one or more embodiments, the scope sheath 105 has a teardrop shaped cross-sectional profile (as best shown in FIGS. 4 and 6). The teardrop shaped cross-sectional profile of the scope sheath 105 results in the central passage 115 having a scope receiving portion 105A (e.g., a generally round portion) and an elongated body receiving portion 105B (e.g., a tapered portion) extending (e.g., contiguously) from the scope receiving portion 105A. The access opening 120 extends through a tip 105C of the elongated body receiving portion 105B. As shown in FIG. 4, preferably, the access opening 120 bisects the tip 105C of the elongated body receiving portion 105B. The scope sheath 105 is an example of a chassis adapted for having an imaging device engaged therewith and the coupling element 110 is an example of an elongated body that may be disposed within the elongated body receiving portion 105B of the scope sheath 105.

Preferably, the scope sheath 105 is made from a thin-walled, flexible and/or conformable material—e.g., an elastomeric material, a heat-shrinkable material, a resilient material or the like. In some embodiments, the scope sheath 105 is made from a material where a visualization scope disposed within the central passage 115 is compressedly engaged by the scope receiving portion 105A. In other embodiments, the scope sheath 105 is made from a material where the scope receiving portion 105A provides a close tolerance fit with a visualization scope disposed within the central passage 115 but does not appreciably provide a compressible force thereon. In still other embodiments, the scope sheath 105 may be made from a rigid material or semi-rigid material. A skilled person will understand that the aforementioned materials may be any material suitable for providing required/desired attributes to the scope sheath 105—e.g., hard plastic, resilient plastic, elastomeric material, heat shrinkable material, metallic material (e.g., metal alloy material) and the like.

In one or more embodiments, the access opening 120 may extend at least partially through an outer wall of the sheath mounting body 130 (e.g., in combination with extending at least partially through the outer wall 122.) In one or more embodiments, the sheath mounting body 130 may be a unitarily-formed component of the scope sheath 105, where the access opening 120 may extend at least partially through the outer wall of the sheath mounting body 130 and/or through the outer wall 122 of the scope sheath 105. It is also disclosed herein that the access opening 120 may extend parallel to, perpendicular to or radially to a centerline longitudinal axis of the scope sheath 105.

The scope receiving portion 105A and the elongated body receiving portion 105B are preferably sized and/or otherwise configured to receive the extension portion of a visualization scope (e.g., the extension portion 10 of the visualization scope 1 discussed above in reference to FIG. 1) and coupling element 110 respectively therein. Furthermore, the scope receiving portion 105A and the elongated body receiving portion 105B are preferably sized and/or otherwise configured such that an extension portion of a visualization scope urges the coupling element 110 into the elongated body receiving portion 105B and/or maintains the coupling element 110 within the elongated body receiving portion 105B.

Preferably, as shown in FIGS. 3-6, the cross-sectional shape and overall configuration of the scope sheath 105 results in an extension portion of a visualization scope (e.g., the extension portion 10 of the visualization scope 1 discussed above in reference to FIG. 1) guiding the coupling element 110 into the elongated body receiving portion 105B of the scope sheath 105 as the extension portion is inserted into and extended along the central passage 115 of the scope sheath 105. In some instances, the coupling element 110 may have an arcuate (i.e., curved) shape such as, for example, due to it being stored in a coiled manner. As such, as the extension portion of the visualization scope is inserted into and extended along the central passage 115 of the scope sheath 105, the coupling element 110 is rotated and self-aligned into the elongated body receiving portion 105B of the scope sheath 105. More specifically, such alignment results in a bisection plane P1 of the coupling element 110 to become nearly aligned with (e.g., extending close to and parallel with) or approximately aligned with (e.g., extending substantially coplanar with) a bisecting plane P2 of the scope sheath 105.

A further benefit of sheath assemblies in accordance with embodiments of the disclosures made herein is the ability to configure a single scope sheath with any one of a plurality of coupling element subassemblies—i.e., coupling element 110 having a cleaning member 125 attached thereto at the distal end portion 110B thereof. For example, each particular coupling element subassembly may have one or more cleaning member attributes and/or one or more coupling element attributes that uniquely define such particular coupling element subassembly. Examples of such cleaning member attributes and coupling element attributes include, but are not limited to, wiper size, wiper geometry, wiper material, coupling element size, coupling element material, coupling element shape and the like.

In view of the disclosures made herein, a skilled person will appreciate that elongated bodies other than a coupling element may be used in combination with a scope sheath. One or more of such other elongated bodies may be used in place of or in addition to a coupling element. Examples of such elongated elements other than a coupling element include but are not limited to an optical fiber cable, a cauterizing body, an irrigation tube, a mechanical device control body and the like. In one or more embodiments, the coupling member 110 may be replaced by or incorporate a structural component adapted to deliver a flowable material (e.g., gas or liquid material) to the second end portion 123 of the scope sheath 105. Alternatively, at least a portion of the space within the scope sheath 105 that surround the coupling element 110 may be used to deliver a flowable material (e.g., gas or liquid material) to the second end portion 123 of the scope sheath 105.

Referring now to FIGS. 7-10, an imaging element cleaning apparatus in accordance with one or more embodiments of the disclosures made (i.e., imaging element cleaning apparatus 101), which comprises the sheath assembly 100 discussed herein in reference to FIGS. 2-10, is shown. The imaging element cleaning apparatus 101 includes a chassis 102, a surgical system attachment body 103, a sheath mount 104, the sheath assembly 100, a rotational movement actuator 118 (e.g., a motor) and an axial movement actuator 124 (e.g., a motor). The rotational movement actuator 118 and the axial movement actuator 124 jointly define a motion control device 128. The chassis 102, the surgical system attachment body 103, the sheath mount 104 and the motion control device 128 may jointly define a drive unit 129.

The surgical system attachment body 103 may be adapted for being engaged with one or more structural components of a robotic surgical system for at least partially securing the imaging element cleaning apparatus 101 thereto. A visualization scope (e.g., the visualization scope 1 discussed above in reference to FIG. 1) is one example of such a structural component of a robotic surgical system. In one or more embodiments, as shown, the surgical system attachment body 103 may be (or comprise) a scope attachment body 106 adapted to be secured to a structural component of a visualization scope (e.g., an extension portion thereof). More specifically, in one or more embodiments, the scope attachment body 106 includes a central passage 126 (i.e., a securement portion) adapted for having an extension portion of a visualization scope disposed therein. The central passage 126 preferably has a centerline longitudinal axis L1 that extends colinearly with a centerline longitudinal axis L2 of the scope sheath 110.

Examples of robotic surgical systems include, but are not limited to, those available from INTUITIVE SURGICAL®, ZIMMER BIOMET®, MEDTRONIC®, STRYKR®, SIEMENS HEALTHINEERS®, JOHNSON&JOHNSON®, and AURIS HEALTH®. Although disclosed in the context of robotic surgical system, imaging element cleaning apparatus and elongated body heath assemblies configured in accordance with one or more embodiments of the disclosures made herein may be implemented in a manner adapted for visualizations scopes configured for used in manual surgical procedures (e.g., laparoscopic surgical procedures). Examples of commercially available visualization scopes (i.e., imaging devices) include, but are not limited to, laparoscopes (i.e., visualization scopes) manufactured under brand names of KARL STORZ®, LINVATEC®, OLYMPUS®, RICHARD WOLF®, STRYKER® and the like.

As shown, the sheath assembly 100 may dock to the drive unit 129 at two locations. The sheath mounting body 130 may be detachably attached to the sheath mount 104 such as by the pins 131 (i.e., protrusions) that each engage a mating groove (i.e., a mating features for providing an interlocked interface) of the scope attachment body 106. Such mating features may be configured for defining/providing a desired angular "clocking" of the sheath assembly 100 relative to the drive unit 129. The interlocked interface either alone or in combination with a supplemental interlocking structure (e.g., a spring-loading structure) may be configured to secure the scope sheath 105 in a positionally and rotationally locked configuration relative to the sheath mount 104. As discussed above in reference to FIGS. 3-6, the sheath assembly 100 may also comprise the coupling element engagement body 135 attached to the first end portion 110A of the coupling element 110 such as via a fastener that secures the coupling element at a fixed location along a length of the coupling element 110. The coupling element engagement body 135 may be located on the coupling element 110 at a prescribed distance from the cleaning member 125. As shown, the coupling element engagement body 135 may be embodied as a tapered body. The coupling element engagement body 135 may be selectively and securely engageable with a mating engagement body 160 of the rotational movement actuator 118. These engagement arrangements of the scope sheath 105 and the coupling element 110 individually and jointly provide for a simple, yet effective and efficient approach for mechanically securing the sheath assembly 100 to the drive unit 129 such as to enable selective interchangeability/replacement of sheath assemblies (e.g., 0-degree wiper sheath assembly or 30-degree wiper sheath assembly).

In one or more embodiments of the disclosures made herein, the imaging element cleaning apparatus 101 may be securely engaged with a visualization scope via the scope attachment body 106 (i.e., a surgical system attachment body), thereby forming a cleaning apparatus enabled visualization scope. To this end, the extension portion of the visualization scope (e.g., the extension portion 10 of the visualization scope 1 of FIG. 1) may extend through the central passage 126 of the scope attachment body 106. The scope attachment body 106 may be in the form of a clamp whereby a securement fastener (e.g., threaded fastener) is used to exert a clamping or other securement force on the extension portion of the visualization scope by the scope attachment body 106, thereby fixedly securing the drive unit 129 to the visualization scope. In view of the disclosures made herein, a skilled person will recognize other approaches for securing the drive unit 129 to the visualization scope. For example, a robotic arm mount of a robotic surgical system is a structural component of a robotic surgical system through which an imaging element cleaning apparatus in accordance with one or more embodiments of the disclosures made herein may be at least partially secured thereto.

As related to the motion control device 128 shown in FIGS. 7-10, the rotational movement actuator 118 is a rotational movement imparting portion thereof and the axial movement actuator 124 is an axial movement imparting portion thereof. Thus, a person of ordinary skill will appreciate that the rotational movement actuator 118 is a first movement actuator adapted to provide rotational movement of a structure coupled to a motion imparting portion thereof and the axial movement actuator 124 is a second movement actuator adapted to provide axial movement of a structure coupled to (e.g., directly attached to) a motion imparting portion thereof. In one or more embodiments, as shown, a mounting portion of the axial movement actuator 124 is attached to the chassis 102 or the surgical system attachment body 103, a mounting portion of the rotational movement actuator 118 is attached to an axial movement imparting portion of the axial movement actuator 124 and the coupling element 110 is attached to a rotational movement imparting portion of the rotational movement actuator 118. The rotational movement actuator 118 can be attached to the chassis 102 or the surgical system attachment body 103 for limiting translational movement of the entire rotational movement actuator 118 to being along a particular axial translation axis—e.g., via a motion control device 127 (e.g., a slide rail) that limits movement to being along an axial translation axis thereof. This arrangement of the motion control device 128 enables independent rotational movement and axial movement of the cleaning member 125 relative to the first end portion 121 of the scope sheath 105 via selective and/or independent actuation of the rotational movement actuator 118 and the axial movement actuator 124. It is contemplated and disclosed herein that, in one or more other embodiments, independent rotational movement and axial movement of the cleaning member 125 may be provided via a single movement actuator or more than two movement actuators. It is also contemplated and disclosed herein that, in one or more other embodiments, such single movement actuator or more than two movement actuators may each be an actuator (e.g., motor) integral with a structural component of a robotic surgical system—e.g., motors integral with a robotic arm of a robotic surgical system controlled by a control apparatus of the robotic surgical system.

In one or more embodiments, as shown, operation of the motion control device 128 (e.g., the rotational movement actuator 118 and the axial movement actuator 124) may be controlled via a movement controller 161—e.g., one or more micro-controllers comprising basic programmable control logic instructions/code/software). For example, in response to the movement controller 161 receiving a cleaning event trigger signal (e.g., via a manual actuation button or system-issued signal), the movement controller 161 issues one or more corresponding signals for causing the motion control device 128 to correspondingly move the cleaning member rotationally and, optionally, axially.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A sheath assembly, comprising:
a sheath including an outer wall having an interior surface that defines a central passage extending along a length of the outer wall, wherein a cross-sectional profile of the central passage is jointly defined by a generally round portion of the outer wall and a tapered portion of the outer wall extending contiguously from the generally round portion, wherein the generally round portion and the tapered portion are integral portions of a single piece of tubing extending over at least a portion of a length of the sheath, wherein an access opening extends from the central passage through a tip of the tapered portion; and
a mounting body attached to an end portion of the sheath adjacent to the access opening, wherein the mounting body is interlockedly engageable with a mating mounting body.

2. The sheath assembly of claim 1 wherein a bisecting axis of the sheath bisects the access opening and the central passage.

3. The sheath assembly of claim 1 wherein the central passage is substantially straight.

4. The sheath assembly of claim 1 wherein the central passage is accessible through an opening in the mounting body.

5. The sheath assembly of claim 4 wherein a bisecting axis of the sheath bisects the access opening and the central passage.

6. The sheath assembly of claim 4 wherein opposing walls of the tapered portion converge to the tip.

7. The sheath assembly of claim 6 wherein the opposing walls are flat.

8. The sheath assembly of claim 4 wherein the central passage is substantially straight.

9. The sheath assembly of claim 1, further comprising:
an elongated member within the central passage, wherein a first end portion of the elongated member extends through the access opening such that a first end of the elongated member is located external to the central passage and a second portion of the elongated member between the access opening and a second end of the elongated member is located within the central passage.

10. The sheath assembly of claim 9 wherein the elongated member has a generally round cross-sectional shape and has an arcuate shape lengthwise.

11. The sheath assembly of claim 9 wherein a bisecting axis of the sheath bisects the access opening and the central passage.

12. The sheath assembly of claim 9 wherein generally flat opposing walls of the tapered portion converge to the tip.

13. The sheath assembly of claim 12 wherein the opposing walls are flat.

14. The sheath assembly of claim 9 wherein the central passage is substantially straight.

15. The sheath assembly of claim 14 wherein the central passage is accessible through an opening in the mounting body.

16. The sheath assembly of claim 9 wherein:
the generally round portion is adapted for having an extension portion of a device inserted therein;
the tapered portion defines an elongated body receiving portion thereof; and
the generally round portion and the tapered portion are jointly configured for causing insertion of the extension portion of the device to urge the second portion of the elongated member into the elongated body receiving portion of the central passage.

17. The sheath assembly of claim 16 wherein a bisecting axis of the sheath bisects the access opening and the central passage.

18. The sheath assembly of claim 16 wherein generally flat opposing walls of the tapered portion converge to the tip.

19. The sheath assembly of claim 18 wherein the opposing walls are flat.

20. The sheath assembly of claim 19 wherein a bisecting axis of the sheath bisects the access opening and the central passage.

21. The sheath assembly of claim 19 wherein generally flat opposing walls of the tapered portion converge to the tip.

22. The sheath assembly of claim 21 wherein a bisecting axis of the sheath bisects the access opening and the central passage.

23. The sheath assembly of claim 22 wherein the central passage is substantially straight.

24. The sheath assembly of claim 16 wherein the central passage is substantially straight.

25. A sheath assembly, comprising:
a sheath including an outer wall having an interior surface that defines a central passage extending along a length of the outer wall, wherein a cross-sectional profile of the central passage is jointly defined by a generally round portion of the outer wall and a tapered portion of the outer wall extending contiguously from the generally round portion, wherein an access opening extends from the central passage through a tip of the tapered portion, and wherein opposing walls of the tapered portion converge together to jointly form the tip; and
a mounting body attached to an end portion of the sheath adjacent to the access opening, wherein the mounting body is interlockedly engageable with a mating mounting body.

26. The sheath assembly of claim 25 wherein the generally round portion and the tapered portion are integral portions of a single piece of tubing extending over at least a portion of a length of the sheath.

27. The sheath assembly of claim 26 wherein a bisecting axis of the sheath bisects the access opening and the central passage.

28. The sheath assembly of claim 26 wherein generally flat opposing walls of the tapered portion converge to the tip.

29. The sheath assembly of claim 28 wherein a bisecting axis of the sheath bisects the access opening and the central passage.

30. The sheath assembly of claim 29 wherein the central passage is substantially straight.

\* \* \* \* \*